(12) United States Patent
Okada

(10) Patent No.: US 7,507,200 B2
(45) Date of Patent: Mar. 24, 2009

(54) DIATHERMIC SNARE, MEDICAL INSTRUMENT SYSTEM USING THE SNARE, AND METHOD OF ASSEMBLING THE MEDICAL INSTRUMENT SYSTEM

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/764,892

(22) Filed: Jan. 26, 2004

(65) Prior Publication Data

US 2004/0158124 A1    Aug. 12, 2004

(30) Foreign Application Priority Data

Jan. 31, 2003   (JP)   ............... 2003-024895

(51) Int. Cl.
*A61B 1/00*   (2006.01)

(52) U.S. Cl. ............. 600/104; 600/121; 600/123; 600/127; 600/129; 606/46; 606/47; 606/113; 606/114; 604/164.13

(58) Field of Classification Search ......... 600/104–107, 600/127, 129; 606/1, 113, 170, 205, 46, 606/47
See application file for complete search history.

(56) References Cited

U.S. PATENT DOCUMENTS 3,805,791 A  *  4/1974  Seuberth et al. ............... 606/47
4,374,517 A  *  2/1983  Hagiwara .................... 600/104
4,615,330 A  *  10/1986  Nagasaki et al. ............ 600/104
4,865,017 A  *  9/1989  Shinozuka ................... 606/127
6,059,719 A  *  5/2000  Yamamoto et al. .......... 600/127
6,068,603 A  *  5/2000  Suzuki ....................... 600/565
6,916,284 B2 *  7/2005  Moriyama ................... 600/127
2001/0053909 A1    12/2001  Nakada et al.

FOREIGN PATENT DOCUMENTS

| DE | 101 26 062 A1 | 12/2001 |
| JP | 56-160516 | 11/1981 |
| JP | 6-9623 | 3/1994 |
| JP | 6-75402 | 10/1994 |
| JP | 2000-116661 | 4/2000 |
| JP | 2001-275933 | 10/2001 |
| JP | 2002-45369 | 2/2002 |

* cited by examiner

*Primary Examiner*—Linda C Dvorak
*Assistant Examiner*—Matthew J Kasztejna
(74) *Attorney, Agent, or Firm*—Scully, Scott, Murphy & Presser, P.C.

(57) ABSTRACT

A loop section has a bending portion at the distal end. The bending portion bends in a direction that intersects the plane formed by the loop section. A diathermic snare is used in combination with an endoscope. When the loop section expands along the inner circumference of an engagement projection of a cap section, the bending portion of the loop section conforms to the corner of the bending portion of the projection.

17 Claims, 9 Drawing Sheets

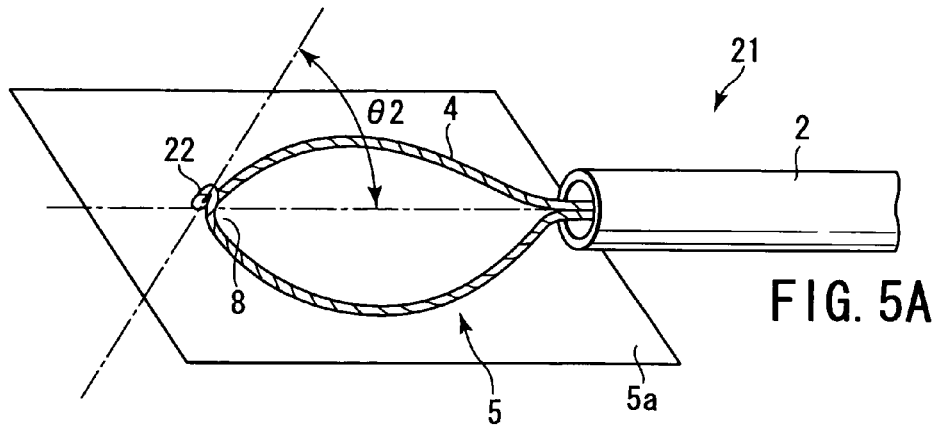
FIG. 5A
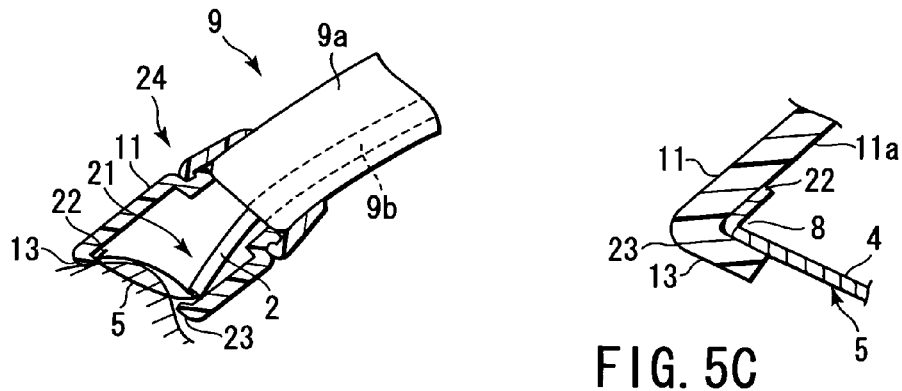
FIG. 5B
FIG. 5C
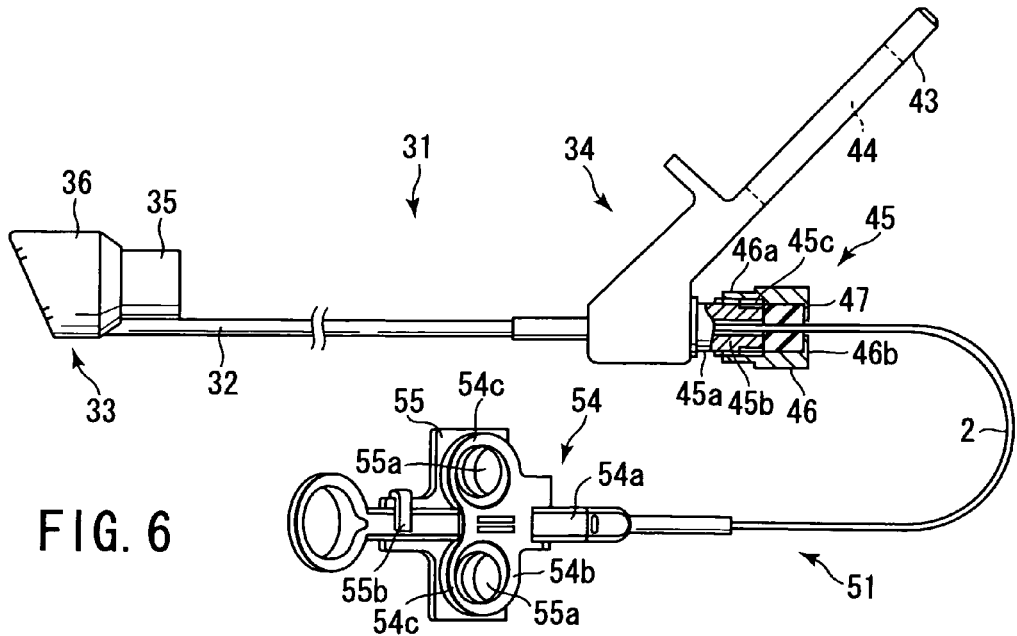
FIG. 6

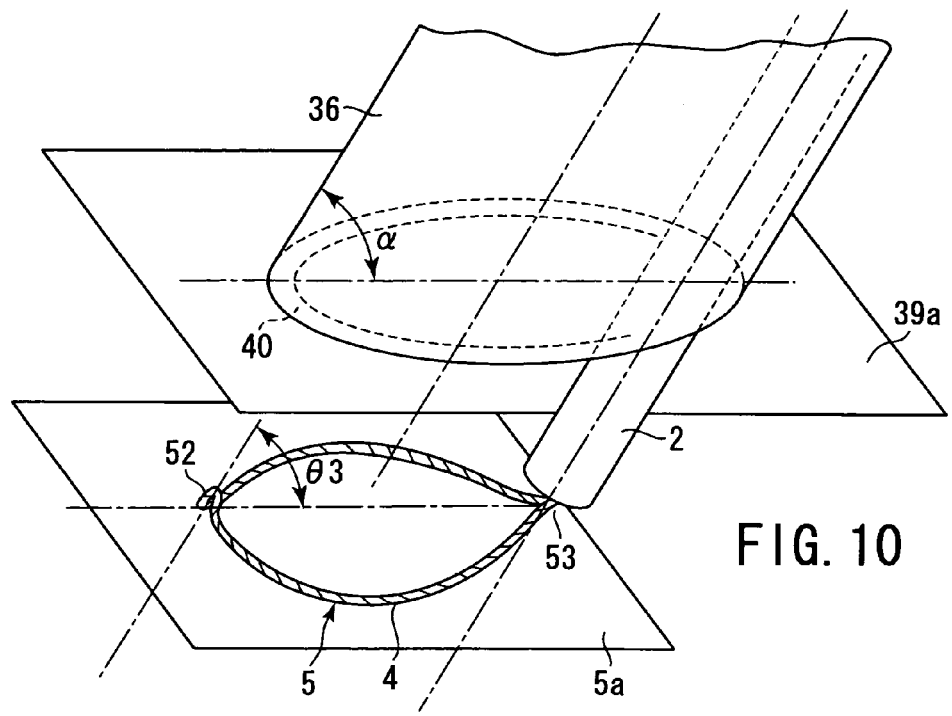
FIG. 10
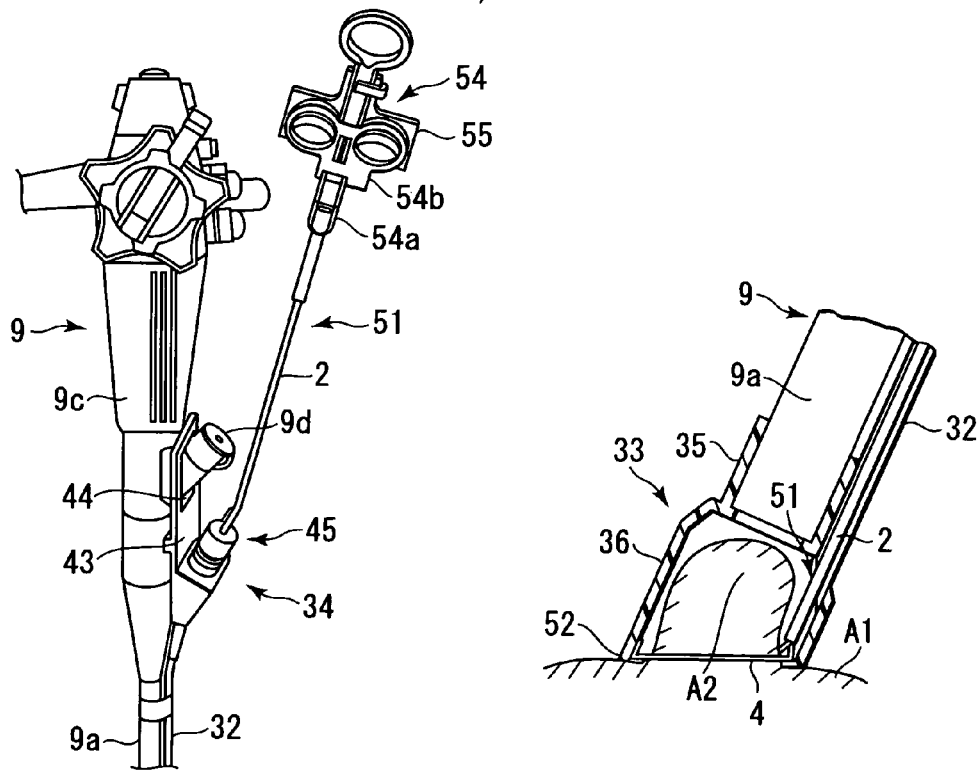
FIG. 11A
FIG. 11B

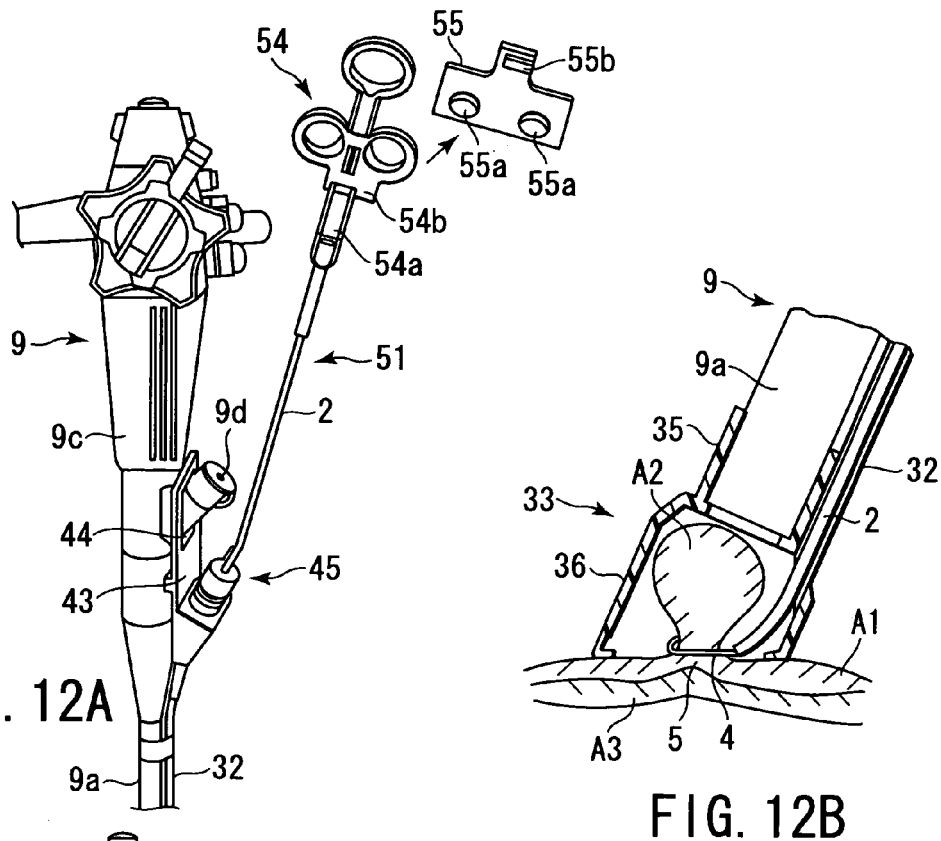
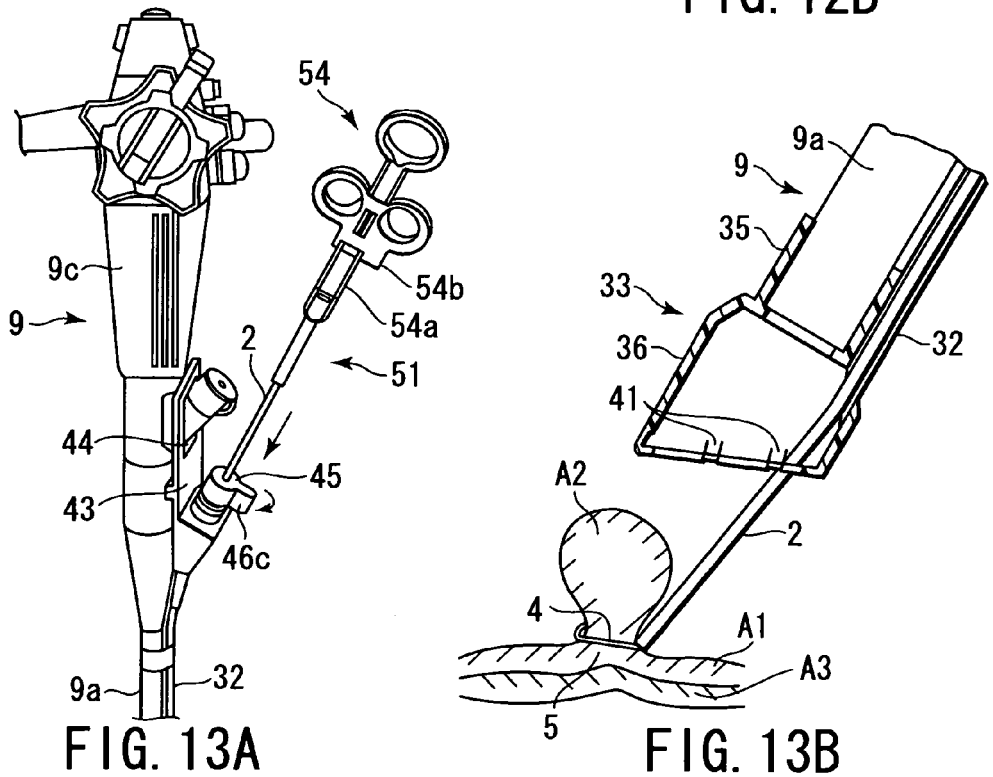
FIG. 12A  FIG. 12B
FIG. 13A  FIG. 13B

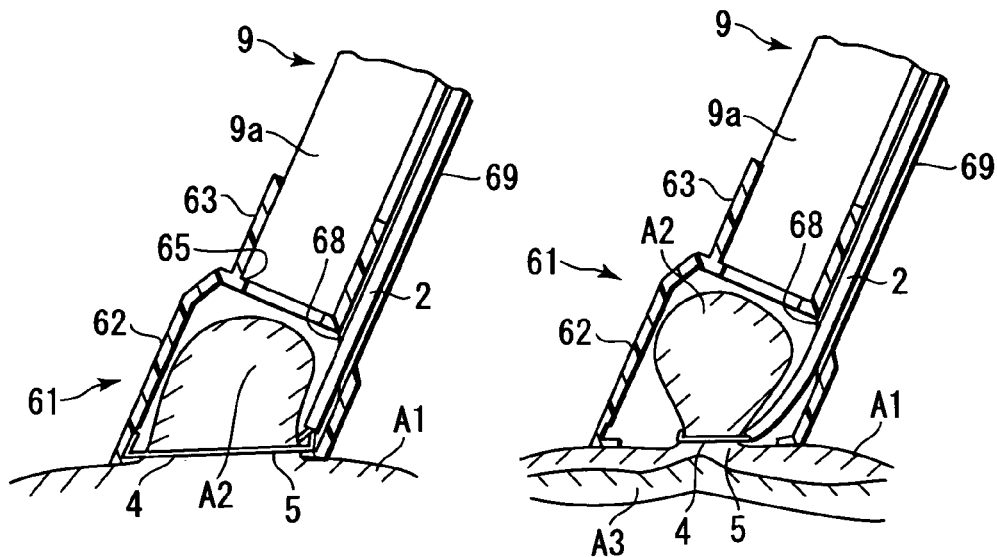
FIG. 17A
FIG. 17B
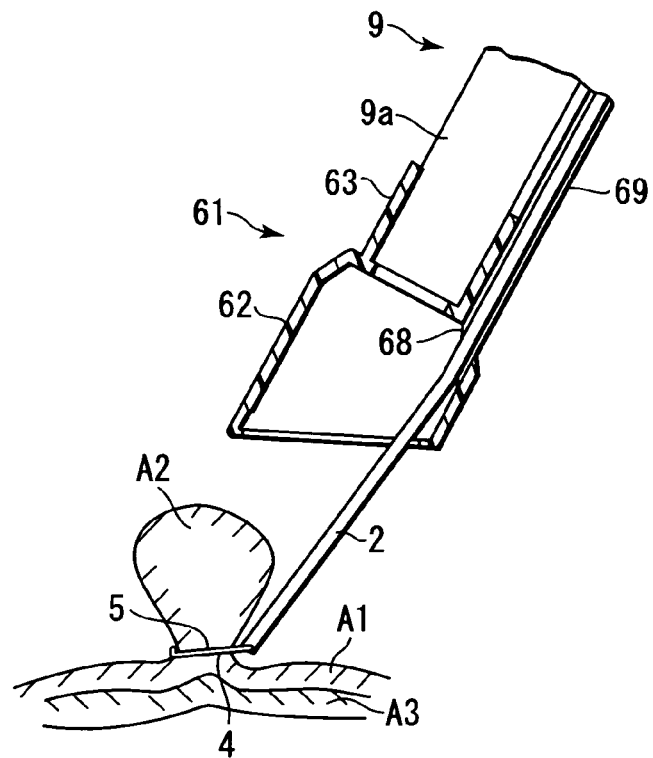
FIG. 17C

DIATHERMIC SNARE, MEDICAL INSTRUMENT SYSTEM USING THE SNARE, AND METHOD OF ASSEMBLING THE MEDICAL INSTRUMENT SYSTEM

CROSS-REFERENCE TO RELATED APPLICATIONS

This application is based upon and claims the benefit of priority from the prior Japanese Patent Application No. 2003-24895, filed Jan. 31, 2003, the entire contents of which are incorporated herein by reference.

BACKGROUND OF THE INVENTION

1. Field of the Invention

The present invention relates to a diathermic snare which sucks a diseased mucous membrane into an almost cylindrical cap that is mounted on the distal end of an inserting section of an endoscope to be brought into a polyp and then removing the polyp, a medical instrument system using the snare, and a method of assembling the medical instrument system.

2. Description of the Related Art

Recently, endoscopic demucosation has widely been performed for early esophagus cancer and gastric cancer. In this demucosation, an operator removes a diseased mucous membrane using an endoscope without opening up the abdomen. One method of the demucosation is disclosed in Jpn. UM Appln. KOKAI Publication No. 6-75402 (patent publication 1) and Jpn. Pat. Appln. KOKAI Publication No. 2001-275933 (patent publication 2). These publications disclose using an endoscope and a diathermic snare in combination. An almost cylindrical hood is mounted on the distal end of an inserting section of the endoscope. The hood has a flange-shaped projection (lug) that projects inward from the inner surface of the distal end of the hood.

The diathermic snare includes an elongated flexible sheath and an operating wire. The operating wire is inserted in the sheath such that it can move forward and backward. A snare wire is connected to the distal end of the operating wire. The snare wire has a loop section that expands almost circularly or elliptically. The loop section projects from the sheath and retracts thereinto as the operating wire moves forward and backward. When the operating wire is pulled toward an operator, the snare wire is pulled and stored in the sheath with its loop section retracted. When the operating wire is pushed forward, the snare wire is projected out of the sheath. The loop section expands like a loop by its own elasticity.

When the diathermic snare is used, it is inserted into a channel of the endoscope. The distal end of the snare projects forward from the channel of the endoscope. In this state, the snare wire projects out of the sheath. The loop section therefore expands like a loop by its own elasticity. The loop section is formed along the flange-shaped projection inside the hood. After that, the diseased mucous membrane to be treated is sucked into the hood and then projected like a polyp. The polyp-like mucous membrane is strangulated at its root by the loop section of the snare and then removed by the passage of power through the snare.

Jpn. Pat. Appln. KOKAI Publication No. 2002-45369 (patent publication 3) discloses a soft tube that is coupled to a hood as disclosed in patent publications 1 and 2. The distal end of the soft tube is connected to a communication opening of the hood to communicate with the inside of the hood. A diathermic snare is inserted into the soft tube. The snare projects a snare wire out of the sheath thereof. Thus, the loop section of the snare wire is expanded like a loop and formed along a flange-shaped projection in the hood. The loop section is then fixed in the hood by an adhesive.

The above method employs a known diathermic snare that is disclosed in Jpn. UM Appln. KOKAI Publication No. 56-160516 (patent publication 4) and Jpn. UM Appln. KOKOKU Publication No. 6-9623 (patent publication 5). The diathermic snare of patent publication 4 has a snare loop that is formed asymmetrically because only one side of the loop is movable. The diathermic snare of patent publication 5 has a snare loop that is formed symmetrically, e.g., elliptically.

BRIEF SUMMARY OF THE INVENTION

According to the present invention, there is provided a diathermic snare used in combination with an endoscope, the endoscope including an inserting section which is inserted into a body cavity and which has a distal end and a proximal end, and a cylindrical cap section mounted on the distal end of the inserting section, the cap section having a distal end, a proximal end and an engagement projection having a bending portion that bends inward at the distal end of the cap section, characterized in that the diathermic snare included, an elongated flexible sheath having a distal end and a proximal end, an operating wire inserted into the sheath so as to move forward and backward and having a distal end and a proximal end, a snare wire coupled to the distal end of the operating wire and having a loop section which expands like a loop, an operating section coupled to the proximal end of the sheath and including a guide member extending in an axial direction of the sheath and a slider which moves forward and backward in the axial direction of the sheath along the guide member and which is coupled to the proximal end of the operating wire, the loop section of the snare wire projecting from the distal end of the sheath, the snare wire expanding like a loop, and the loop section expanding along an inner circumference of the engagement projection when the slider moves toward along the guide member, and the loop section being stored in the sheath when the slider moves backward along the guide member, and a bending portion provided at the distal end of the loop section, the bending portion bending in a direction that intersects a plane formed by the loop section and conforming to a corner of the bending portion of the engagement projection when the loop section expands along the inner circumference of the projection.

According to the present invention, there is provided a medical instrument system using a diathermic snare and an endoscope in combination with each other, the endoscope including an inserting section which is inserted into a body cavity and which has a distal end and a proximal end, and a cylindrical cap section mounted on the distal end of the inserting section, the cap section having a distal end, a proximal end and an engagement projection having a bending portion that bends inward at the distal end of the cap section, characterized in that the diathermic snare comprises, an elongated flexible sheath having a distal end and a proximal end, an operating wire inserted into the sheath so as to move forward and backward and having a distal end and a proximal end, a snare wire coupled to the distal end of the operating wire and having a loop section which expands like a loop, an operating section coupled to the proximal end of the sheath and including a guide member extending in an axial direction of the sheath and a slider which moves forward and backward in the axial direction of the sheath along the guide member and which is coupled to the proximal end of the operating wire, the loop section of the snare wire projecting from the distal end of the sheath, the snare wire expanding like a loop, and the loop section expanding along an inner circumference of the engagement projection when the slider moves toward along the guide member, and the loop section being stored in the sheath when the slider moves backward along the guide member, and a bending portion provided at the distal end of the loop section, the bending portion bending in a direction that intersects a plane formed by the loop section and conforming to a corner of the bending portion of the engagement projection when the loop section expands along the inner circumference of the projection.

Preferably, the cap section has a main body that is made of transparent materials.

Preferably, the engagement projection has a flange section that projects toward an inner surface of the cap section in proximity to a leading edge of the cap section.

Preferably, the cap section has a fixing section at the proximal end thereof, the fixing section being fixed to a distal end of the endoscope, and the medical instrument system further comprises a soft tube having an open distal end and an open proximal end, the soft tube being arranged alongside the inserting section of the endoscope when the fixing section is fixed to the distal end of the endoscope, and the open distal end communicating with an inside of the cap section.

Preferably, the bending portion of the loop section bends at a bend angle which is almost perpendicular to the plane formed by the loop section.

Preferably, the bending portion of the loop section bends at an acute bend angle corresponding to an acute angle to the plane formed by the loop section.

Preferably, the cap section has an inclined plane corresponding to a plane of the distal end of the cap section which is inclined to the axial direction of the sheath, and the bending portion of the loop section bends in the axial direction of the sheath.

Preferably, the plane formed by the loop section has an inclination angle that is set such that the plane is almost parallel to the inclined plane of the cap section.

Preferably, the inclined plane of the cap section inclines at an acute angle in the axial direction of the sheath, and the bending portion of the loop section bends at a bend angle that is equal to an inclination angle of the inclined plane.

Preferably, the loop section has a diameter that is equal to an inside diameter of the cap section.

Preferably, the loop section rotates around an axis of the sheath.

According to the present invention, there is provided a method of assembling a medical instrument system using a diathermic snare and an endoscope in combination with each other, the endoscope including an elongated inserting section which is inserted into a body cavity and which has a distal end and a proximal end, and a cylindrical cap section mounted on the distal end of the inserting section, the cap section having a distal end, a proximal end, an engagement projection having a bending portion that bends inward at the distal end of the cap section, a fixing section provided at the proximal end of the cap section and fixed to a distal end of the endoscope, and a soft tube having an open distal end and an open proximal end, the soft tube being arranged alongside the inserting section of the endoscope when the fixing section is fixed to the distal end of the endoscope, and the open distal end communicating with an inside of the cap section, the diathermic snare including an elongated flexible sheath having a distal end and a proximal end, an operating wire inserted into the sheath so as to move forward and backward and having a distal end and a proximal end, a snare wire coupled to the distal end of the operating wire and having a loop section which expands like a loop, an operating section coupled to the proximal end of the sheath and including a guide member extending in an axial direction of the sheath and a slider which moves forward and backward in the axial direction of the sheath along the guide member and which is coupled to the proximal end of the operating wire, the loop section of the snare wire projecting from the distal end of the sheath, the snare wire expanding like a loop, and the loop section expanding along an inner circumference of the engagement projection when the slider moves toward along the guide member, and the loop section being stored in the sheath when the slider moves backward along the guide member, and a bending portion provided at the distal end of the loop section, the bending portion bending in a direction that intersects a plane formed by the loop section and conforming to a corner of the bending portion of the engagement projection when the loop section expands along the inner circumference of the projection, and the plane formed by the loop section inclining in the axial direction of the sheath and the loop section rotating around an axis of the sheath, characterized by comprising, a diathermic snare inserting step of mounting the cap section on the endoscope, then inserting the diathermic snare into the tube, and projecting the distal end of the sheath forward from the cap section, a loop section projecting step of projecting the loop section from the sheath while the distal end of the sheath is projected from the cap section, a loop section direction adjusting step of rotating the loop section around an axis of the sheath when necessary and adjusting a direction of the loop section, a retracting step of retracting the loop section into the cap section, a cap section pressing step of pressing a leading edge of the cap section against an object, and a loop section setting step of pushing the sheath to bring the loop section into intimate contact with the engagement projection and expanding the loop section circularly along the engagement projection.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5A is a perspective view showing a distal end of the diathermic snare according to a second embodiment of the present invention.

FIG. 5B is a longitudinal sectional view of a principal part of the diathermic snare that is used in combination with an endoscopic hood.

FIG. 5C is a longitudinal sectional view of a principal part of the diathermic snare whose distal-end projection is fitted on the inner wall of a cap section.

FIG. 6 is a side view of an endoscopic demucosation instrument according to a third embodiment of the present invention.

FIG. 10 is an illustration of a configuration of the snare wire of the endoscopic demucosation instrument according to the third embodiment.

FIG. 11A is a perspective view of the periphery of an operator side operating section of the endoscope that is operated to suck a mucous membrane into the cap section of the endoscopic demucosation instrument according to the third embodiment and raise a removal portion of the mucous membrane.

FIG. 11B is a longitudinal sectional view of the periphery of an open distal end of the cap section the endoscopic demucosation instrument.

FIG. 12A is a perspective view of the periphery of an operator side operating section of the endoscope that is operated to draw up a removal portion tightly fastened by the snare wire of the endoscopic demucosation instrument according to the third embodiment.

FIG. 12B is a longitudinal sectional view of the periphery of an open distal end of the cap section the endoscopic demucosation instrument.

FIG. 13A is a perspective view of the periphery of an operator side operating section of the endoscope that is operated to draw up a removal portion tightly fastened by the snare wire of the endoscopic demucosation instrument according to the third embodiment and remove the removal portion while causing a radio-frequency current to flow through the snare wire.

FIG. 13B is a longitudinal sectional view of the periphery of an open distal end of the cap section the endoscopic demucosation instrument.

FIG. 17A is a longitudinal sectional view showing a state in which the open distal end of the cap section is pressed on a mucous membrane to suck the mucous membrane when the mucous membrane is removed by the medical instrument according to the fourth embodiment.

FIG. 17B is a longitudinal sectional view showing a state in which the snare wire is retracted into the sheath and the removal portion of the mucous membrane is fastened tightly at the root.

FIG. 17C is a longitudinal sectional view showing a state in which the removal section fastened tightly by the snare wire is taken and separated from the cap section.

DETAILED DESCRIPTION OF THE INVENTION

Figure 1:
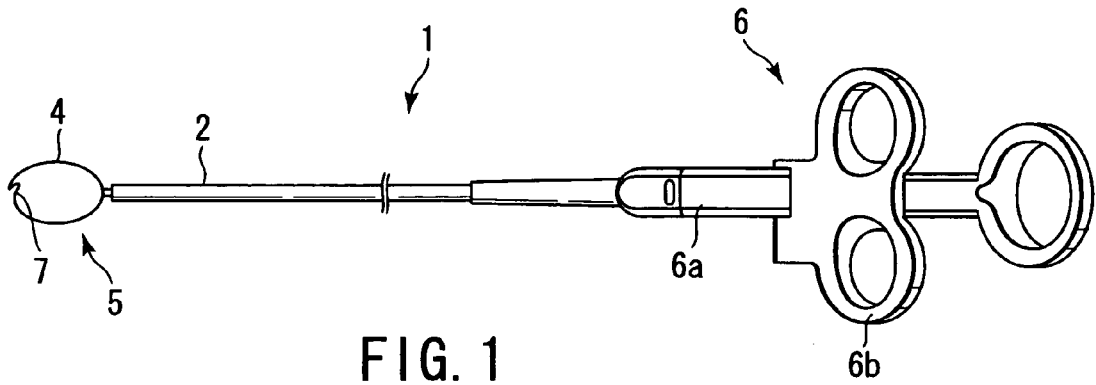
FIG. 1 is a plan view showing a diathermic snare according to a first embodiment of the present invention.
Figure 2:
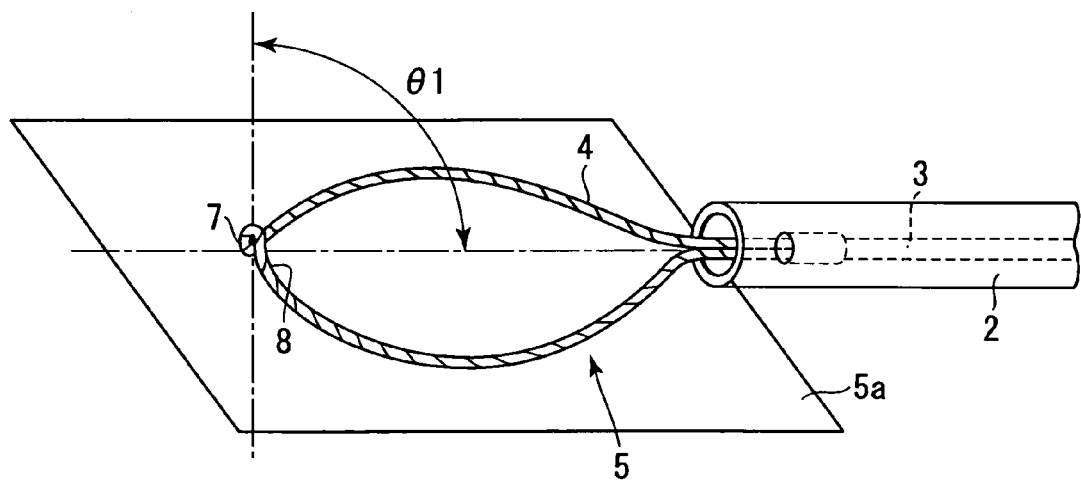
FIG. 2 is a perspective view showing a distal end of the diathermic snare according to the first embodiment of the present invention.

A first embodiment of the present invention will now be described with reference to FIGS. 1 to 4E. FIG. 1 shows a diathermic snare 1 according to the first embodiment. The diathermic snare 1 includes an elongated flexible sheath 2. The sheath 2 has electrical insulating characteristic. Referring to FIG. 2, an operating wire 3 is inserted into the sheath 2 such that it can move back and forth. A snare wire 4 is connected to the distal end of the wire 3. The snare wire 4 has an almost elliptic loop section 5.

The sheath 2 has an operating section 6 nearest to the operator. The operating section 6 has an axial guide member 6a and a slider 6b. The slider 6b can slide back and forth in the axial direction of the guide member 6a. The guide member 6a is coupled to the proximal end of the sheath 2. The guide member 6a has a wire insertion hole (not shown) inside. The wire 3 is inserted into the wire insertion hole. The proximal end of the wire 3 is connected to the slider 6b.

When the slider 6b slides back and forth along the guide member 6a or in the axial direction, the wire 3 is driven to move back and forth in its axial direction. The movement of the wire 3 allows the loop section 5 of the snare wire 4 to project from and retract into the distal end of the sheath 2. If the slider 6b moves forward along the guide member 6a, the loop section 5 projects from the sheath 2 and expands almost elliptically by its own expandability. If the slider 6b moves backward along the guide member 6a, the loop section 5 is retracted and stored in the sheath 2.

The snare wire 4 has a distal-end projection 7 at the distal end of the loop section 5. The projection 7 bends and projects in the direction that intersects the plane 5a of the loop section 5, or at a bend angle of θ1 to the plane 5a in the first embodiment. The bend angle of θ1 is about 90 degrees and, in other words, the projection 7 bends at almost right angles. The projection 7 has two wire bending portions 8 at the root thereof. The wire bending portions 8 are each bent at almost right angles to the plane 5a of the loop section 5.

The diathermic snare 1 according to the first embodiment is used in combination with an endoscope 9 as illustrated in FIGS. 4A to 4E. The endoscope 9 includes an elongated inserting section 9a that is to be inserted into a body cavity. The inserting section 9a has a channel 9b inside. The channel 9b extends from the distal end of the inserting section 9a to the proximal end thereof. The snare 1 is inserted into the body cavity through the channel 9b of the endoscope 9.

An endoscopic hood 10 is mounted on the distal end of the inserting section 9a. The hood 10 has a transparent cap section 11 that is almost cylindrical. The cap section 11 has an almost cylindrical endoscope mounting section 12 at the proximal end. The endoscope mounting section 12 is detachably fixed to the distal end of the inserting section 9a. A flange-shaped small-diameter projection (lug) 13 projects inward from the inner surface of the cap section 11 in proximity to the leading edge of the cap section 11.

An operation of the diathermic snare 1 so configured will now be described. The removal of a mucous membrane A1 from a body cavity by the snare 1 will be discussed with reference to FIGS. 4A to 4E. First, an operator fixes the endoscopic hood 10 to the distal end of the inserting section 9a of the endoscope 9 and inserts the inserting section 9a into the body cavity. The operator moves the open distal end of the cap section 11 of the endoscopic hood 10 toward the target mucous membrane A1.

Figure 4A:
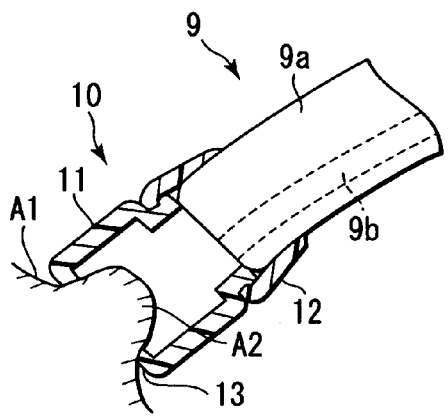
FIG. 4A is a longitudinal sectional view of a principal part of the diathermic snare according to the first embodiment, which is operated to pull a mucous membrane into a hood by negative pressure and raise a removal portion of the mucous.

As shown in FIG. 4A, the operator presses the distal end of the cap section 11 against the mucous membrane A1 and sucks the mucous membrane A1 through the channel 9b of the endoscope 9. The mucous membrane A1 is pulled into the hood 10 by negative pressure and the removal portion A2 of the mucous membrane A1 is bulged.

Figure 4B:
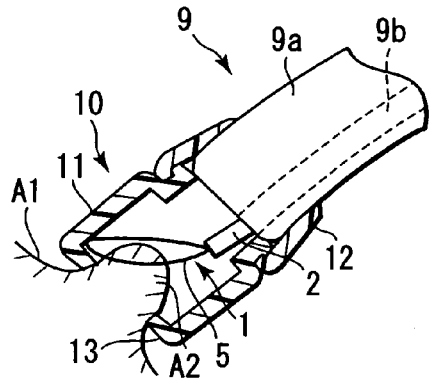
FIG. 4B is a longitudinal sectional view of a principal part of the diathermic snare according to the present invention, which is inserted to pay a snare wire out of a flexible sheath.

The operator inserts the diathermic snare 1 into the channel 9b. The loop section 5 of the snare 1 is retracted into the sheath 2, and the sheath including the loop section 5 is inserted into the channel 9b. The operator projects the distal end of the sheath 2 from the distal end of the channel 9b. The slider 6b slides forward along the guide member 6a. The operator pays the loop section 5 out of the sheath 2 as shown in FIG. 4B. The loop section 5 paid out of the sheath 2 expands almost elliptically by its own expandability.

Figure 3:
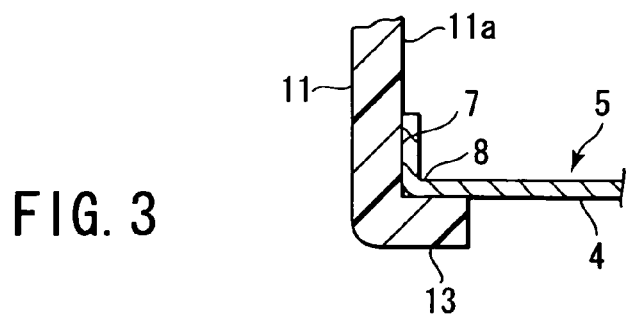
FIG. 3 is a longitudinal sectional view of a principal part of the diathermic snare according to the first embodiment, the distal-end projection of which is fitted on the inner wall of a cap section.
Figure 4C:
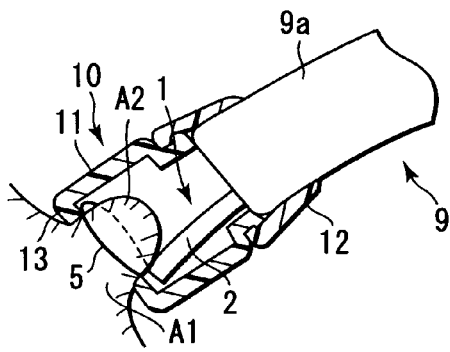
FIG. 4C is a longitudinal section of a principal part of the diathermic snare according to the present invention, in which a loop is set at the root of the removal portion of the bulged mucous membrane.

The pay-out of the loop section 5 from the sheath 2 continues until the end distal of the loop section 5 runs against the projection 13 at the distal end of the cap section 11 as illustrated in FIG. 4B. The operator pushes the sheath 2 forward to open the loop section 5. The loop section 5 is set at the root of the bulged removal portion A2 of the mucous membrane A1 as shown in FIG. 4C. The distal-end projection 7 of the loop section 5 is brought into intimate contact with the corner of the inner wall 11a of the cap section 11 as shown in FIG. 3. The loop section 5 is firmly engaged with the top of the projection 13.

Figure 4D:
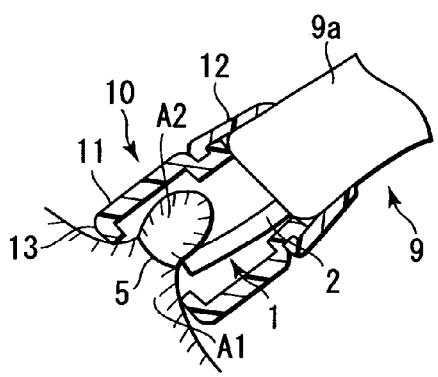
FIG. 4D is a longitudinal section of a principal part of the diathermic snare according to the present invention, in which the loop is pulled into the flexible sheath and the removal portion is being drawn up.

Then, the operator moves the slider 6b backward along the guide member 6a. As shown in FIG. 4D, the operator retracts the loop section 5 into the sheath 2 and draws up the removal portion A2 of the mucous membrane A1.

Figure 4E:
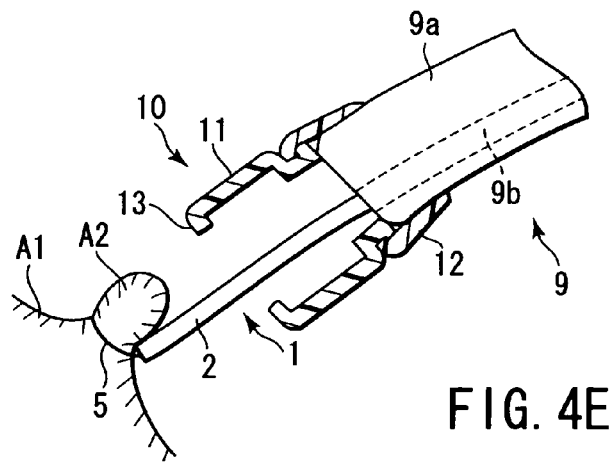
FIG. 4E is a longitudinal section of a principal part of the diathermic snare according to the present invention, in which the loop is pulled into the flexible sheath and the removal portion has been drawn up.

Referring to FIG. 4E, the operator projects the sheath 2 forward from the channel 9b and separates the mucous membrane A1 from the cap section 11. The operator causes a radio-frequency current to flow through the loop section 5 to remove the removal portion A2 of the mucous membrane A1. The removed portion A2 is sucked through the channel 9b of the endoscope 9 and stored in the hood 10 by the suction force. The removed portion A2 stored in the hood 10 is taken out of the body cavity and collected together with the endoscope 9.

The diathermic snare 1 with the above configuration brings about the following advantages. In the snare 1, the distal-end projection 7 is provided at the distal end of the loop section 5 and bent almost perpendicularly to the plane 5a formed by the loop section 5. In endoscopic demucosation, the loop section 5 expands along the inner circumference of the cap section 11 of the hood 10. The shape of the bent projection 7 of the loop section 5 conforms to that of the corner of the inner wall of the cap section 11. Thus, the loop section 5 is properly arranged on the flange-shaped projection 13 of the cap section 11 such that the projection 7 conforms to the corner of the inner wall of the cap section 11. It is thus possible to prevent the loop section 5 from bumping against the projection 13 in an inappropriate state. Consequently, a looping operation of looping the loop section 5 around the cap section 11 can be performed easily and reliably.

FIGS. 5A to 5C illustrate a second embodiment of the present invention. The second embodiment is a modification to the configuration of a medical instrument using the diathermic snare 1 according to the first embodiment (see FIGS. 1 to 4E) in combination with the endoscope 9.

A diathermic snare 21 according to the second embodiment includes an acute-angled distal-end projection 22. This projection 22 bends at a bend angle of θ2 to the plane 5a formed by the loop section 5 and the bend angle is set at less than 90 degrees as shown in FIG. 5A. The second embodiment differs from the first embodiment in that the distal end of the distal-end projection 22 is inclined closer to the sheath 2 than the root thereof.

Referring to FIG. 5B, the snare 21 is used in combination with an endoscopic hood 24 having an inclined plane 23 that corresponds to the leading edge of the cap section 11 that is inclined in the insertion direction of the endoscope 9. The inclination angle of the inclined plane 23 is substantially equal to the bend angle of θ2 of the distal-end projection 22. The hood 24 has a flange-shaped small-diameter projection 13 that projects inward along the inclined plane 23 as shown in FIG. 5C.

The above acute-angled distal-end projection 22 is provided at the distal end of the loop section 5. As described above, the bend angle of θ2 of the projection 22 to the plane 5a is set at less than 90 degrees. In a combination of the diathermic snare 21 with the endoscope 9, when the loop section 5 expands along the inner circumference of the cap section 11, the bending portion of the distal-end projection 22 conforms to the corner of the inner wall of the cap section 11. The distal-end projection 22 is prevented from bumping against the corner of the inner wall of the cap section 11 in an inappropriate state. The loop section 5 can thus be arranged properly to overlap the flange-shaped projection 13 of the cap section 11. Consequently, a looping operation of looping the loop section 5 around the cap section 11 can easily and reliably be performed.

FIGS. 6 to 13B illustrate a third embodiment of the present invention. FIG. 6 illustrates an endoscopic demucosation instrument 31 according to the third embodiment. The endoscopic demucosation instrument 31 is used in combination with a diathermic snare 51. The principal part of the snare 51 has substantially the same configuration as that of the snare 1 according to the first embodiment (see FIGS. 1 to 4E).

Figure 7A:
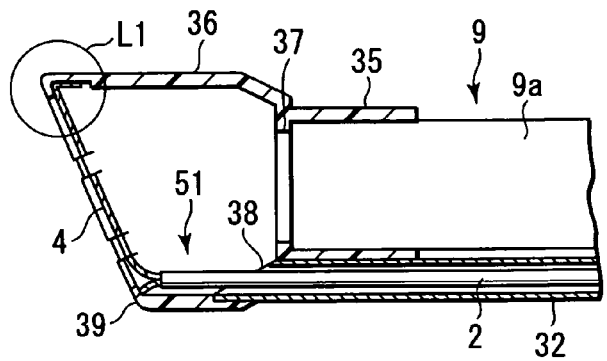
FIG. 7A is a longitudinal sectional view showing a configuration in which a cap section of the endoscopic demucosation instrument according to the third embodiment is fixed to the distal end of an inserting section of an endoscope.

The endoscopic demucosation instrument 31 has an elongated soft tube 32. Referring to FIG. 7A, the tube 32 is externally disposed alongside the inserting section 9a of an endoscope 9. The length of the tube 32 is almost equal to or greater than the effective length of the inserting section 9a. The tube 32 is fixed to the inserting section 9a by medical tape or the like.

The tube 32 has a distal-end coupling section 33 at the distal end and a proximal-end coupling section 34 at the proximal end. The distal-end coupling section 33 is coupled to the distal end of the inserting section 9a of the endoscope 9. The proximal-end coupling section 34 is coupled to an operator-side operating section 9c of the endoscope 9 as illustrated in FIG. 11A.

The distal-end coupling section 33 has an almost cylindrical endoscope mounting section 35 and an almost cylindrical cap section 36 having a large diameter. The endoscope mounting section 35 is detachably fitted on the outer circumference of the distal end of the inserting section 9a. The cap section 36 is disposed at the distal end of the endoscope mounting section 35. Referring to FIG. 7A, the endoscope mounting section 35 has an endoscope engagement section 37 at the distal end. The endoscope engagement section 37 projects inward from the distal end of the endoscope mounting section 35.

When the endoscopic demucosation instrument 31 is fixed to the endoscope 9, the distal end of the inserting section 9a of the endoscope 9 is inserted into the endoscope mounting section 35. As shown in FIG. 7A, the insertion 9a is pushed until its distal end bumps against the endoscope engagement section 37. The endoscope mounting section 35 is detachably fixed to the distal end of the inserting section 9a while the distal end of the inserting section 9a is not inserted into the cap section 36.

There is a flange-shaped step between the proximal end of the cap section 36 and the distal end of the endoscope mounting section 35. The step has a communicating section 38 that communicates with the inside of the cap section 36. The tube 32 is provided outside the endoscope mounting section 35. The distal end of the tube 32 is coupled to the communicating section 38 and hermetically fixed to both the endoscope mounting section 35 and cap section 36 by bonding, welding or the like. The distal end of the tube 32 opens to the inside of the cap section 36. The tube 32 and cap section 36 are connected such that their axes are almost parallel with each other. The open distal end of the tube 32 is close to the inner wall of the cap section 36.

The cap section 36 has an inclined plane 39 at the leading edge. The inclined plane 39 inclines toward the inserting direction of the endoscope 9. The leading edge of the cap section 36 has a flange-shaped projection 40 having a small diameter. The projection 40 projects inward along the inclined plane 39. The communicating section 38 is located in a position (trailing edge) of the inclined plane 39 in which an amount of projection of the projection 40 is small.

Figure 8A:
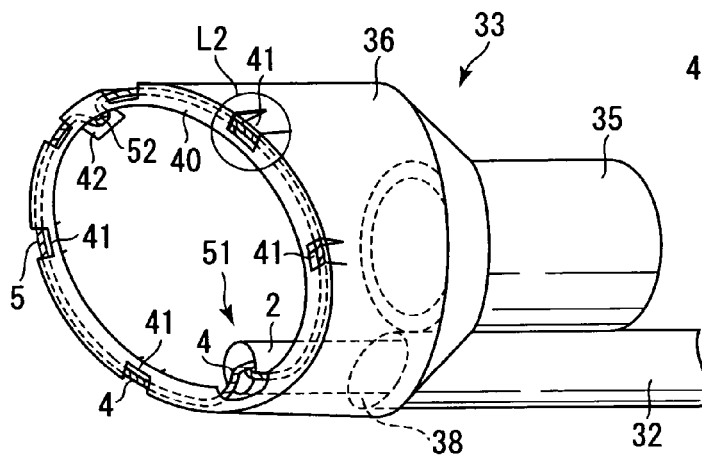
FIG. 8A is a perspective view of a snare wire of the endoscopic demucosation instrument according to the third embodiment, which is held by a projection of the cap section.
Figure 8B:
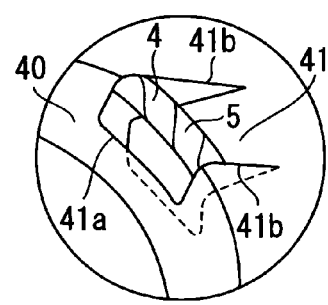
FIG. 8B is a perspective view of an enlarged principal part of the portion L2 shown in FIG. 8A.

Referring to FIG. 8A, a plurality of engagement sections 41 are provided in a bending portion between the periphery of the cap section 36 and the projection 40. The engagement sections 41 are arranged along the circumferential direction of the cap section 36. The engagement sections 41 are each cut and bulged inward. In other words, as shown in FIG. 8B, the engagement sections 41 each have a lateral notch 41a located in almost the central part of the projection 40 and two longitudinal notches 41b arranged from both ends of the notch 41a to the periphery of the cap section 36. The engagement sections 41 are each cut and bulged such that a portion between the lateral notch 41a and the two longitudinal notches 41b is inclined inward. The endoscopic demucosation instrument 31 is used in combination with the diathermic snare 51. Referring to FIG. 8A, the loop section 5 of the snare 51 expands along the inner circumference of the cap section 36. The snare wire 4 is pressed by the outer surface of each of the engagement sections 41 and supported alternately by the projection 40 and each of the engagement sections 41.

Figure 7B:
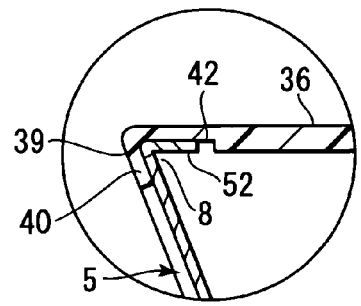
FIG. 7B is a longitudinal sectional view of an enlarged principal part of the portion L1 shown in FIG. 7A.

The inclined plane 39 of the cap section 36 shown in FIG. 7A has a recess 42 shown in FIG. 7B. The recess 42 is located in a position (leading edge) of the inner wall of the inclined plane 39 where an amount of projection is large. The loop section 5 of the diathermic snare 51 expands along the inner circumference of the cap section 36. A distal-end projection 52 of the loop section 5, which will be described later, is fitted into the recess 42.

Figure 9:
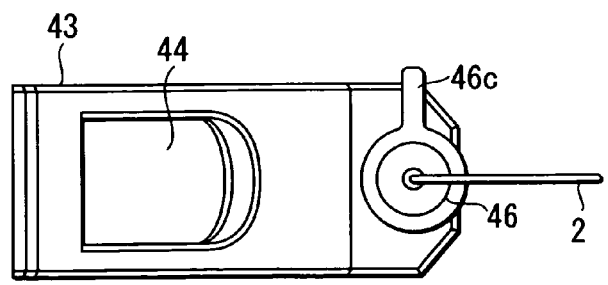
FIG. 9 is a plan view of an operator side hook section of a soft tube of the endoscopic demucosation instrument according to the third embodiment.
Figure 14:
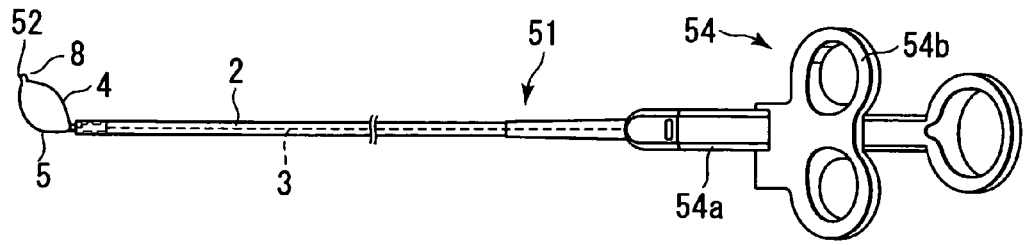
FIG. 14 is a side view showing a medical instrument according to a fourth embodiment of the present invention.

The proximal-end coupling section 34 has a hook section 43 on the operator side of the tube 32. The hook section 43 is engaged with the proximal end of the endoscope 9 and has an engagement hole 44 as shown in FIG. 9. Referring to FIG. 11A, part of the operator-side operating section 9c of the endoscope 9, e.g., a forceps stopper 9d is inserted into the engagement hole 44 and engaged therewith. The hook section 43 is therefore hooked and fixed on a portion of the endoscope 9 in proximity to the forceps stopper 9d.

The proximal-end coupling section 34 has a diathermic snare fixing section 45. The fixing section 45 has a cylindrical base member 45a. The base member 45a is fixed to one end of the proximal-end coupling section 34 and has a communicating hole 45b that communicates with the tube 32 inside. A male thread section 45c is formed on the outer surface of the base member 45a. A rotating ring 46 is fitted on the male thread section 45c. The rotating ring 46 has a screw hole 46a at the distal end, and the male thread section 45c is fitted on the screw hole 46a. The base member 45a has an elastic tube holder 46b at the proximal end. The elastic tube holder 46b includes an elastic tube 47 and holds it therein. The elastic tube 47 is held with its distal end in contact with the base member 45a.

Referring to FIG. 9, a knob 46c protrudes from the outer circumference of the rotating ring 46 in its radial direction. When the rotating ring 46 is rotated by the knob 46c, the male thread 45c of the base member 45a is fitted in the screw hole 46a of the rotating ring 46. For example, when the rotating ring 46 is rotated by the knob 46c in its tightening direction, the elastic tube 47 in the elastic tube holder 46b is crushed and elastically deformed in its inside hole narrowing direction. Thus, the sheath 2 of the diathermic snare 51 inserted into the elastic tube 47 can be disengaged. The rotating ring 46 is rotated by the knob 46c in a direction (loosening direction) opposite to the tightening direction to loosen the ring 46. In this case, the crushed elastic tube 47 is restored and the sheath 2 is disengaged, with the result that the sheath 2 can move forward and backward.

The diathermic snare 51 is removably inserted into the tube 32. The principal part of the snare 51 has substantially the same configuration as that of the principal part of the snare 1 according to the first embodiment (see FIGS. 1 to 4E). The sheath 2 of the snare 51 is inserted into the tube 32 from the diathermic snare fixing section 45 of the proximal-end coupling section 34. The distal end of the sheath 2 of the snare 51 inserted into the tube 32 projects into the cap section 36 from the communicating section 38 as illustrated in FIGS. 7A and 8A. The snare wire 4 is paid out of the sheath 2 and then held on the projection 40 of the cap section 36 as shown in FIGS. 8A and 8B.

The snare wire 4 of the diathermic snare 51 is formed as shown in FIG. 10. The snare wire 4 has a distal-end projection 52. The distal-end projection 52 projects from the distal end of the almost elliptical loop section 5 and bends in a direction that intersects the plane 5a formed by the loop section 5. In the third embodiment, the distal-end projection 52 bends at an acute bend angle of θ3 to the plane 5a. The bend angle of θ3 is substantially equal to the inclination angle of α of the inclined plane 39 of the leading edge of the cap section 36.

The diathermic snare 51 has a bending portion 53 that bends toward the proximal end of the loop section 5. The bending portion 53 is set as follows. The sheath 2 of the snare 51 is inserted into the tube 32 and projected from the communicating section 38. Referring to FIG. 10, the plane 5a is formed almost parallel to the inclined plane 39a including the projection 40 of the cap section 36. Thus, the loop section 5 expands along the inner circumference of the projection 40 to be disposed with reliability.

The diathermic snare 51 has an operator-side operating section 54 at the proximal end. The operating section 54 includes an axial guide member 54a and a slider 54b that can move forward and backward in the axial direction of the guide member 54a. The guide member 54a is coupled to the proximal end of the sheath 2. The guide member 54a has a wire insertion hole (not shown) through which the wire 3 is inserted.

The proximal end of the wire 3 is connected to the slider 54b. As the slider 54b moves forward and backward in the axial direction of the guide member 54a, the wire 3 is driven to move forward and backward in the same direction. Thus, the loop section 5 of the snare wire 4 projects and retreats from the distal end of the sheath 2. For example, when the slider 54b moves forward along the guide member 54a, the loop section 5 projects from the sheath 2 and then expands almost elliptically by its own expandability. When the slider 54b moves backward along the guide member 54a, the loop section 5 is retracted and stored in the sheath 2.

The operating section 54 has a regulation member 55. The regulation member 55 regulates the to-and-fro motion of the slider 54b. The regulation member 55 has two convex portions 55a and one fixing portion 55b. The convex portions 55a are fitted into a finger holding section 54c of the slider 54b. The fixing portion 55b fixes the regulation member 55 to the guide member 54a. When the regulation member 55 is fitted to the operating section 54, it regulates the to-and-fro motion of the slider 54b. The snare wire 4 is therefore regulated such that it does not move in the cap section 36.

An operation of the diathermic snare 51 according to the third embodiment will now be described. The removal of a mucous membrane A1 using the endoscopic demucosation instrument 31 will be discussed. First, an operator attaches the endoscopic demucosation instrument 31 to the endoscope 9. The distal-end coupling section 33 of the instrument 31 is attached to the distal end of the inserting section 9a of the endoscope 9. The operator disposes the tube 32 alongside the inserting section 9a and fixes the tube 32 to the inserting section 9a by medical tape or the like. After that, the operator hooks and fixes the hook section 43 of the proximal-end coupling section 34 of the instrument 31 to a portion near to the forceps stopper 9d of the endoscope 9, as illustrated in FIG. 11A.

The operator inserts the endoscope 9 and endoscopic demucosation instrument 31 into the body cavity. The operator moves the open distal end of the cap section 36 of the instrument 31 to a target mucous membrane removal portion A2 while observing the removal portion A2 through the endoscope 9.

Referring to FIG. 11B, the operator presses the open distal end of the cap section 36 against the mucous membrane A1. The sucking force from a sucking apparatus (not shown) is exerted on the inside of the cap section 36 through the channel 9b of the endoscope 9. The operator sucks the mucous membrane A1 into the cap section 36. The mucous membrane A1 is pulled into the cap section 36 by negative pressure and the removal portion A2 is bulged.

As shown in FIG. 12A, the operator detaches the regulation member 55 from the operating section 54 of the snare 51 and moves the slider 54b of the operating section 54 backward along the guide member 54a. In this operation, the loop section 5 of the snare wire 4 is detached from the engagement sections 41 of the cap section 36 and pulled into the sheath 2, as shown in FIG. 12B. Thus, the loop section 5 is reduced in size and consequently, the root of the removal portion A2 of the mucous membrane A1 is fastened tightly by the loop section 5.

Referring to FIG. 13A, the operator holds the knob 46c of the fixing section 45 and rotates the rotating ring 46 to loosen the elastic tube 47. The sheath 2 is disengaged and pushed forward.

The push operation causes the distal end of the sheath 2 to project from the cap section 36 as shown in FIG. 13B. The operator takes the removal portion A2 that is fastened tightly by the loop section 5 out of the cap section 36 and separates it therefrom. The operator inserts an ultrasonic probe or the like (not shown) into the channel 9b of the endoscope 9 and examines the conditions of the mucous membrane A1 and muscle layer A3 using the ultrasonic probe or the like. He or she confirms that the muscle layer A3 is not caught in the portion fastened tightly by the loop section 5. It is thus possible to remove the mucous membrane A1 safely.

In the state shown in FIG. 13B, the operator draws up the removal portion A2 by the loop section 5 and causes a radio-frequency current to flow through the snare wire 4 to remove the mucous membrane A1. After the ultrasonic probe or the like is pulled out of the channel 9b, the portion A2 removed from the mucous membrane A1 is sucked by the channel 9b and held in the cap section 36. The removed portion A2 in this state is taken out of the body cavity together with the endoscope 9.

The diathermic snare 51 configured as described above brings about the following advantages. In the endoscopic demucosation instrument 31, the distal-end projection 52 of the loop section 5 of the diathermic snare 51 is bent at substantially the same angle as the inclination angle of the cap section 36. The proximal end of the loop section 5 is bent. The inclined plane 39 including the projection 40 of the cap section 36 and the plane 5a formed by the loop section 5 are almost parallel to each other. If the endoscopic demucosation instrument 31 is used in combination with the snare 51, the loop section 5 expands along the inner circumference of the cap section 36. As shown in FIG. 8A, the distal-end projection 52 and loop section 5 are brought into intimate contact with the inner surface of the cap section 36 and the projection 40. The loop section 5 can thus be mounted on the projection 40 with reliability. Consequently, a looping operation of looping the loop section 5 around the cap section 36 can easily and reliably be performed as in the first embodiment.

FIGS. 14 to 17C illustrate a fourth embodiment of the present invention. A diathermic snare 51 of the fourth embodiment has the same configuration as that of the snare 51 of the third embodiment (see FIGS. 6 to 13B). In the fourth embodiment, the snare 51 is used in combination with an endoscopic hood 61 shown in FIG. 15A.

The endoscopic hood 61 includes an almost cylindrical transparent cap section 62 and an almost cylindrical endoscope mounting section 63. The endoscope mounting section 63 fixes the hood 61 detachably to the distal end of the inserting section 9a of an endoscope 9. The cap section 62 and endoscope mounting section 63 differ in both outside and inside diameters and are connected to each other by means of a tapered flange 64.

The endoscope mounting section 63 has an endoscope engagement section 65 (see FIG. 17A) at the distal end. The endoscope engagement section 65 projects inward from the outer surface of the distal end of the endoscope mounting section 63. In order o fix the hood 61 to the endoscope 9, the distal end of the inserting section 9a of the endoscope 9 is inserted into the mounting section 63. The inserting section 9a is pushed into the mounting section 63 until its distal end runs against the endoscope engagement section 65. Thus, the distal end of the inserting section 9a is not inserted into the cap section 62 but the endoscope mounting section 63 of the hood 61 is fixed to the distal end of the inserting section 9a.

Moreover, the leading edge of the cap section 62 has an inclined plane 66 that is inclined in the insertion direction of the endoscope 9. The cap section 62 has a flange-shaped, small-diameter projection 67 at the distal end. The projection 67 projects inward from the outer surface of the distal end of the cap section 62 along the inclined plane 66. A diathermic snare wire 4, which is paid out of a snare sheath 2 of the snare 51, is held on the projection 67.

There is a flange-shaped step between the proximal end of the cap section 62 and the distal end of the endoscope mounting section 63. The step has a communicating section 68 (see FIG. 17A) that communicates with the inside of the cap section 62. The communicating section 68 is located in the shortest portion of the cap section 62 in the inserting direction. A soft tube 69 is provided outside the endoscope mounting section 63. The diathermic snare 51 can be inserted into the soft tube 69. The distal end of the tube 69 is coupled to the communicating section 68 described above. The distal end of the tube 69 is hermetically fixed to both the endoscope mounting section 63 and cap section 62 by means of bonding, welding or the like. The distal end of the tube 69 opens to the inside of the cap section 62.

In the connecting portion of the tube 69 and cap section 62, the major axis of the tube 69 and the axis of the cap section 62 are almost parallel to each other. The open distal end of the tube 69 is located close to the inner wall of the cap section 62.

In the fourth embodiment, the distal-end projection 52 of the snare 51 is bent to the plane 5a formed by the loop section 5 (see FIG. 10). The bend angle of the distal-end projection 52 is substantially equal to the inclination angle of α of the inclined leading edge of the cap section 62. The plane 5a is bent such that it is almost parallel to the inclined plane 39 (see FIG. 10) including the projection 67 of the cap section 62.

In the fourth embodiment, the sheath 2 and the guide member 54a of the operating section 54 are coupled to each other such that they can mutually be rotated. If the operating section 54 rotates relative to the sheath 2, its rotation is transmitted to the snare wire 4 through the wire 3. The wire 3 has a high torque transfer characteristic.

An operation of the diathermic snare 51 according to the fourth embodiment will now be described. The removal of a mucous membrane A1 using the snare 51 will be discussed. First, an operation of looping the snare wire 4 around the projection 67 of the cap section 62 will be discussed.

Figure 15A:
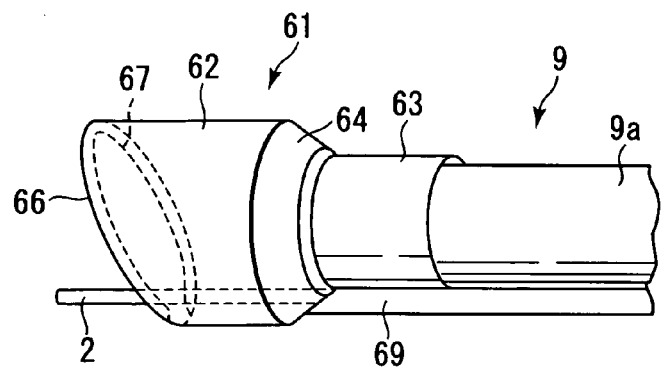
FIG. 15A is a perspective view showing a state in which the sheath of a diathermic snare of the medical instrument according to the fourth embodiment is inserted into a soft tube and projected out of a cap section when a snare wire is looped around a flange-shaped projection of the cap section.

An operator attaches and fixes the endoscopic hood 61 the distal end of the inserting section 9a of the endoscope 9. In this state, the operator inserts the endoscope 9 and endoscopic hood 61 into a body cavity and the inserts the sheath 2 of the snare 5 into the tube 69. Referring to FIG. 15A, the operator projects the distal end of the snare 51 outside the cap section 62.

Figure 15B:
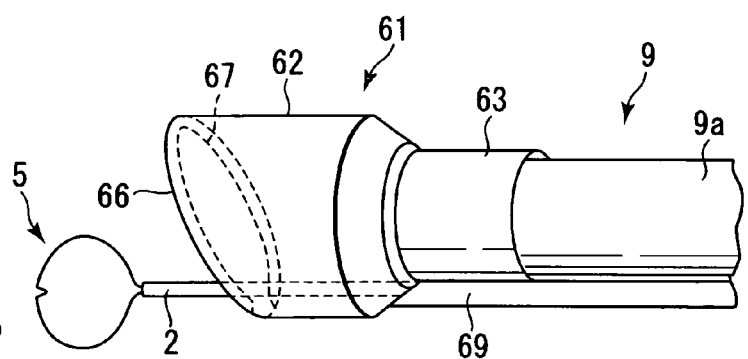
FIG. 15B is a perspective view showing a state in which the loop of the diathermic snare project out of the sheath thereof.
Figure 15C:
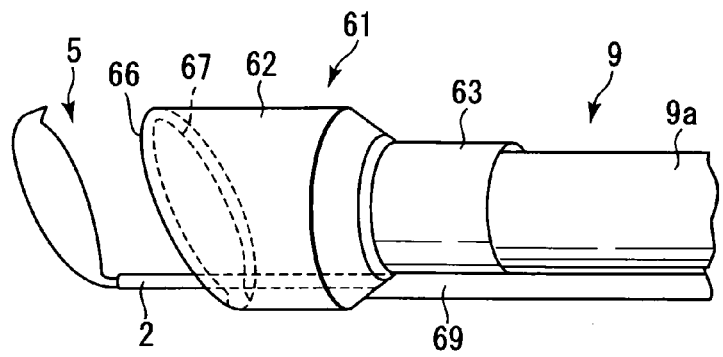
FIG. 15C is a perspective view showing a state in which an operating section is rotated to set the plane of the loop parallel to the circumference of the open distal end of the cap section.

Referring to FIG. 15B, the operator projects the loop section 5 from the sheath 2. If the plane 5a formed by the loop section 5 is not parallel to the plane 39 of the projection 67 of the cap section 62, the operator rotates the operating section 54 to make the plane 5a parallel to the plane 39 as illustrated in FIG. 15C.

Figure 16A:
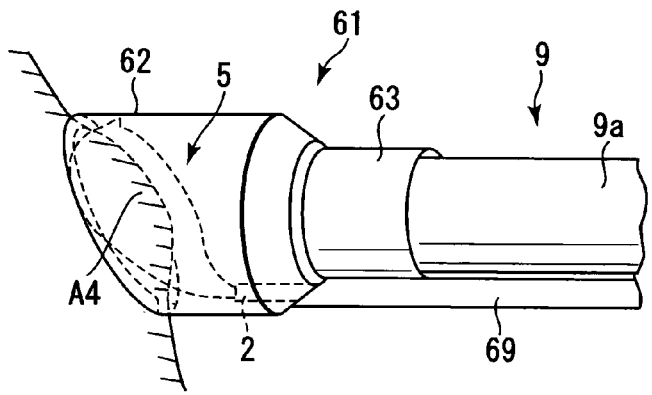
FIG. 16A is a perspective view showing a state in which the open distal end of the cap section is softly pressed on a mucous membrane to suck the mucous membrane.
Figure 15D:
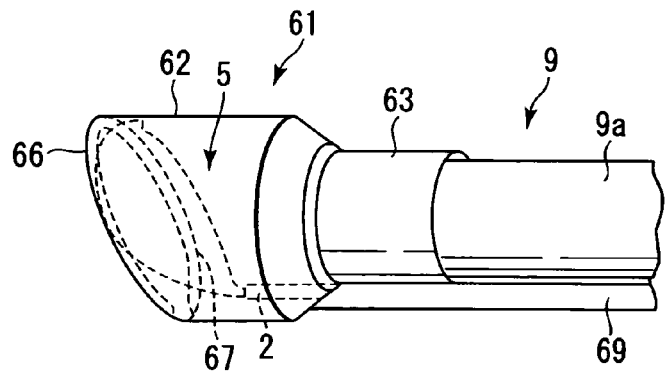
FIG. 15D is a perspective view of the loop that is stored in the cap section by retracting the sheath.

Referring to FIG. 15D, the operator pulls the sheath 2 to store the loop section 5 in the cap section 62. Referring to FIG. 16A, he or she softly presses the open distal end of the cap section 62 on an arbitrary mucous membrane A4 and sucks the mucous membrane A4.

Figure 16B:
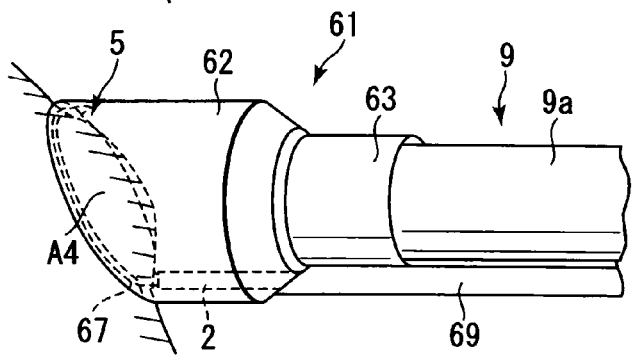
FIG. 16B is a perspective view showing a state in which the sheath is pushed out and the loop is pressed on the circumference of the open distal end of the cap section to set the loop on the flange-shaped projection of the cap section.
Figure 16C:
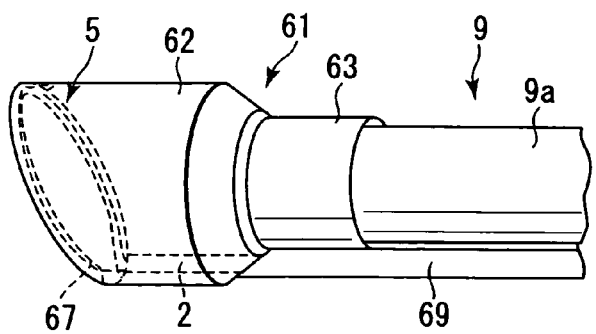
FIG. 16C is a perspective view showing a state in which the suction is released and the cap section is separated from the mucous membrane to complete the looping operation.

Referring to FIG. 16B, the operator pushes out the sheath 2 and presses the loop section 5 on the projection 67 of the cap section 62. The loop section 5 is therefore mounted on the projection 67. The operator releases the suction and, as shown in FIG. 16C, he or she separates the cap section 62 from the mucous membrane A4 to complete the looping operation.

In order to remove the mucous membrane A1, the operator moves the open distal end of the cap section 62 to the mucous membrane A1 and presses it against the mucous membrane A1 as shown in FIG. 17A. The mucous membrane A1 is sucked into the cap section 62 by the sucking force from a sucking apparatus (not shown) through the channel 9b of the endoscope 9. The mucous membrane A1 is sucked into the cap section 62 by negative pressure and the removal portion A2 of the mucous membrane A1 is bulged.

The operator moves the slider 54b backward along the guide member 54a and pulls the snare wire 4 into the sheath 2 as shown in FIG. 17B. The root of the removal portion A2 is fastened tightly by the snare wire 4. The sheath 2 is pushed in and, as shown in FIG. 17C, it is projected out of the cap section 62. The operator takes the removal portion A2 fastened tightly by the snare wire 4 from the cap section 62 and separates it therefrom.

The operator inserts an ultrasonic probe or the like into the channel 9b of the endoscope 9 and examines the conditions of the mucous membrane A1 and muscle layer A3 using the ultrasonic probe or the like. The operator confirms that the muscle layer A3 is not caught in the removal portion A2 fastened tightly by the snare wire 4. It is thus possible to remove the mucous membrane A1 safely.

In the state shown in FIG. 17C, the operator draws up the removal portion A2 and causes a radio-frequency current to flow through the snare wire 4 to remove the mucous membrane A1. The operator pulls the ultrasonic probe or the like out of the channel 9b. The removed mucous membrane A1 is sucked through the channel 9b and held in the cap section 62. The operator takes the mucous membrane A1 out of the body cavity and collects it together with the endoscope 9.

The diathermic snare 51 configured as described above brings about the following advantages. In the fourth embodiment, the distal-end projection 52 of the loop section 5 of the snare 51 is bent at substantially the same angle as the inclination angle of the cap section 62 of the endoscopic hood 61. The proximal end of the loop section 5 is bent, and the plane 5a formed by the loop section 5 is almost parallel to the plane 39 including the projection 67 of the cap section 62. The wire 3 has a high torque transfer characteristic. By the above-described method, the operator can perform a looping operation of looping the loop section 5 of the snare 51 around the cap section 62 easily and reliably for endoscopic demucosation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical instrument system using a diathermic snare and an endoscope in combination with each other, the endoscope including a substantially cylindrical cap section mounted on a distal end of an elongated inserting section which is to be inserted into a body cavity, wherein the cap section has a flange-shaped projection that projects inward from the inner circumference surface of the distal end;

wherein the diathermic snare comprises:

a flexible sheath;

an operation wire inserted into the flexible sheath to be movable forwards and backwards: and a snare wire coupled to the distal end of the operation wire; and wherein, when the endoscope and the diathermic snare is used in combination with each other, a loop section which expands to one of a substantially circular or elliptical loop when the snare wire is projected from the sheath is formed, the loop section expanding along the inner circumference of the cap section, the medical instrument system comprising a distal-end projection which projects in the direction that intersects a plane of the loop at the distal end of the loop section and is fitted on an inner wall of the cap section when the loop section expands along the inner circumference of the cap section.

2. The medical instrument system according to claim 1, wherein the cap section has a main body that is made of transparent materials.

3. The medical instrument system according to claim 1, wherein the flange-shaped projection projects toward an inner surface of the cap section in proximity to a leading edge of the cap section.

4. The medical instrument system according to claim 1, wherein:

the cap section has a fixing section at the proximal end thereof, the fixing section being fixed to a distal end of the endoscope; and the medical instrument system further comprises a soft tube having an open distal end and an open proximal end, the soft tube being arranged alongside the inserting section of the endoscope when the fixing section is fixed to the distal end of the endoscope, and the open distal end communicating with an inside of the cap section.

5. The medical instrument system according to claim 1, wherein the bending distal-end projection of the loop section bends at a bend angle which is almost perpendicular to the plane formed by the loop section.

6. The medical instrument system according to claim 1, wherein the bending distal-end projection of the loop section bends at an acute bend angle corresponding to an acute angle to the plane formed by the loop section.

7. The medical instrument system according to claim 1, wherein:

the cap section has an inclined plane corresponding to a plane of the distal end of the cap section which is inclined to the axial direction of the sheath; and a bending portion of the loop section bends in the axial direction of the sheath.

8. The medical instrument system according to claim 7, wherein the plane formed by the loop section has an inclination angle that is set such that the plane is almost parallel to the inclined plane of the cap section.

9. The medical instrument system according to claim 7, wherein:

the inclined plane of the cap section inclines at an acute angle in the axial direction of the sheath; and the bending portion of the loop section bends at a bend angle that is equal to an inclination angle of the inclined plane.

10. The medical instrument system according to claim 1, wherein the loop section has a diameter that is equal to an inside diameter of the cap section.

11. The medical instrument system according to claim 1, wherein the loop section rotates around an axis of the sheath.

12. The diathermic snare according to claim 1, wherein the distal-end projection is bendable at a substantially right angle with respect to the plane formed by the loop section.

13. The diathermic snare according to claim 1, wherein the distal-end projection is bendable at an acute angle with respect to the plane formed by the loop section.

14. A method of assembling a medical instrument system using a diathermic snare and an endoscope in combination with each other, the method comprising:

a diathermic snare inserting step of mounting a cylindrical cap section on a distal end of an inserting section of the endoscope, and projecting a distal end of a sheath of the diathermic snare forward from the cap section;

a loop section projecting step of projecting the loop section from the sheath while the distal end of the sheath is projected from the cap section;

a loop section direction adjusting step of rotating the loop section around an axis of the sheath when necessary and adjusting a direction of the loop section;

a retracting step of retracting the loop section into the cap section;

a cap section pressing step of pressing a leading edge of the cap section against an object; and a loop section setting step of pushing the sheath to bring the loop section into tight contact with the engagement projection and expanding the loop section circularly along the engagement projection such that a distal end bent section of the loop section bent in a direction that intersects a plane formed by the loop section is disposed at an intersection of the engagement projection and an inner wall of the cylindrical cap section.

15. A diathermic snare used in combination with an endoscope, the endoscope including an inserting section which is inserted into a body cavity and which has a distal end and a proximal end, and a cylindrical cap section mounted on the distal end of the inserting section, the cap section having a distal end, a proximal end and an engagement projection having a bending portion that bends inward at the distal end of the cap section, wherein the diathermic snare comprises:

an elongated flexible sheath having a distal end and a proximal end;

an operating wire inserted into the sheath so as to move forward and backward and having a distal end and a proximal end;

a snare wire coupled to the distal end of the operating wire and having a loop section which expands like a loop;

an operating section coupled to the proximal end of the sheath and including a guide member extending in an axial direction of the sheath and a slider which moves forward and backward in the axial direction of the sheath along the guide member and which is coupled to the proximal end of the operating wire; the loop section of the snare wire projecting from the distal end of the sheath, the snare wire expanding like a loop, and the loop section expanding along an inner circumference of the engagement projection when the slider moves toward along the guide member; and the loop section being stored in the sheath when the slider moves backward along the guide member; and a bending portion provided at the distal end of the loop section, the bending portion ending in a direction that intersects a plane formed by the loop section and conforming to a corner of the bending portion of the engagement projection when the loop section expands along the inner circumference of the projection;

wherein the cap section has an inclined plane corresponding to a plane of the distal end of the cap section which is inclined to the axial direction of the sheath and the bending portion of the loop section bends in the axial direction of the sheath.

16. The medical instrument system according to claim 15, wherein the plane formed by the loop section has an inclination angle that is set such that the plane is almost parallel to the inclined plane of the cap section.

17. The medical instrument system according to claim 15, wherein:

the inclined plane of the cap section inclines at an acute angle in the axial direction of the sheath; and the bending portion of the loop section bends at a bend angle that is equal to an inclination angle of the inclined plane.

* * * * *